United States Patent
Doskotz et al.

(10) Patent No.: US 10,722,434 B2
(45) Date of Patent: Jul. 28, 2020

(54) LIQUID COOLING COMPOSITIONS

(71) Applicant: Symrise AG, Holzminden (DE)

(72) Inventors: Eike Doskotz, Erftstadt (DE); Thorsten Hielscher, Höxter (DE); Andreas Engelbrecht, Holzminden (DE); Andrea Püttcher, Bevern (DE); Arnold Machinek, Holzminden (DE)

(73) Assignee: Symrise AG, Holzminden (DE)

( * ) Notice: Subject to any disclaimer, the term of this patent is extended or adjusted under 35 U.S.C. 154(b) by 246 days.

(21) Appl. No.: 15/574,010

(22) PCT Filed: May 10, 2016

(86) PCT No.: PCT/EP2016/060474
§ 371 (c)(1),
(2) Date: Nov. 14, 2017

(87) PCT Pub. No.: WO2016/184731
PCT Pub. Date: Nov. 24, 2016

(65) Prior Publication Data
US 2019/0175465 A1    Jun. 13, 2019

(30) Foreign Application Priority Data
May 15, 2015 (EP) .................... 15167910

(51) Int. Cl.
| A61K 8/34 | (2006.01) |
| A61K 8/37 | (2006.01) |
| A61K 31/045 | (2006.01) |
| A61Q 11/00 | (2006.01) |
| A61Q 19/00 | (2006.01) |
| A61K 8/11 | (2006.01) |

(52) U.S. Cl.
CPC .......... *A61K 8/34* (2013.01); *A61K 8/11* (2013.01); *A61K 8/37* (2013.01); *A61Q 11/00* (2013.01); *A61Q 19/00* (2013.01); *A61K 2800/244* (2013.01); *A61K 2800/5922* (2013.01)

(58) Field of Classification Search
None
See application file for complete search history.

(56) References Cited

U.S. PATENT DOCUMENTS

| 3,023,253 A | 2/1962 | Bain et al. |
| 2012/0128744 A1* | 5/2012 | Sorge ................. A23G 4/06 424/401 |

FOREIGN PATENT DOCUMENTS

| DE | 2608226 A1 * | 9/1977 |
| EP | 1 332 772 A2 | 8/2003 |
| EP | 2 033 688 A2 | 3/2009 |
| EP | 2 457 554 A1 | 5/2012 |
| JP | 2002119264 A * | 4/2002 |
| WO | 2007/128723 A1 | 11/2007 |
| WO | 2013/171015 A2 | 11/2013 |

OTHER PUBLICATIONS

Jabloner, H., B. I. Dunbar, and A. J. Hopfinger. "A molecular approach to flavor synthesis. I. Menthol esters of varying size and polarity." Journal of Polymer Science: Polymer Chemistry Edition 18.10 (1980): 2933-2940.*
Eccles, R. "Menthol and related cooling compounds." Journal of Pharmacy and Pharmacology 46.8 (1994): 618-630.*

* cited by examiner

*Primary Examiner* — Bethany P Barham
*Assistant Examiner* — Peter Anthopolos
(74) *Attorney, Agent, or Firm* — Dilworth & Barrese, LLP

(57) ABSTRACT

Suggested are liquid cooling compositions, containing
(a) L-Menthol,
(b) D-Menthol, and
(c) at least one further cooling agent, selected from the group consisting of isomenthol, menthyl acetate (L), menthyl acetate (D), menthyl acetate (iso), acetic acid menthyl lactate (iso) and acetic acid menthyl lactate (neo)
with the proviso that in case that component (c) represents Isomenthol, the compositions do not contain any alkanediols.

3 Claims, No Drawings

LIQUID COOLING COMPOSITIONS

FIELD OF THE INVENTION

The invention is in the field of cosmetics and relates to cooling compositions based on menthol which are liquid over a wide range of temperature, cosmetic products and, particularly, capsules containing these, their use for the production of cosmetic products and a process for the cooling of the skin and of the mucous membranes.

STATE OF THE ART

Menthol is a naturally occurring active agent which causes a cooling effect when brought into contact with the mucous membranes, specifically, the oral mucosa. Menthol and numerous subsequently developed menthol compounds which have, in part, a significantly increased cooling effect are thus widely used in the pharmaceutical, cosmetic and food industries. Menthol that is found in natural sources, for example, in peppermint oil, is present in the form of four diastereomeric pairs of enantiomers, of which only the main component, (−)-menthol or L-menthol, has the desired taste and other sensory properties, as already described in J. Am. Chem. Soc, Vol. 39 (8), 1917, pp. 1515-1525. Particularly, the melting points of these various forms are between 33 and 43° C., as described in Archly der Pharmazle, 307 (7), 1974, pp 497-503. Accordingly, the melting point of the stable α-form is between 42 and 43° C.

Due to this position of the melting points, L-menthol and most menthol compounds can be delivered to the end user both as a melt that is kept liquid in heated containers, and also in the form of crystals or other congealed molded bodies such as granular materials, pastilles, flakes and the like. In general, all solids which have a melting point of barely above the ambient temperature have a strong tendency to cake and to agglomerate, such as L-menthol and any substances that are structurally related to menthol. The processing of such material that does not comply with the specification, however, involves a substantial additional effort. If pure L-menthol, or menthol compounds, is to be sold as a solid, i.e. as a material that has not been treated with additives such as, for example, separating agents, it must be ensured that the product reaches the end user in pourable form, either by an unbroken cold chain or by the way the product is shaped.

Menthol is commercially available, for example, in the form of large crystals having a thickness from 1 to 3 mm at a length from 0.5 to 3 cm. They are traditionally grown in small amounts from naturally obtained peppermint oil, where the oil is allowed to crystallise in troughs or tubs in cold storage for many days. These crystals have a ready pourability only at a low filling height, but they increasingly agglomerate visibly at an increased load and/or an increased temperature. The technical effort to realise the crystallisation, the separation and the purification of the crystals and the low space/time profit of such a long-term process render it unattractive for industrial use.

Conventional methods of the state of the art attempt to improve the handling of menthol by means of shaping, specifically by means of the particle size.

DE 2530481 relates to a device for crystallising substances, particularly of optically active menthol compounds which form coarse needle-shaped or rod-shaped crystals under crystallisation conditions. The crystallisation process, which must be carried out discontinuously, is performed by means of a particular stirring device that prevents an agglomeration of the crystals in the crystal suspension. Finally, the value product is isolated by a centrifuge and dried in a dryer.

The two patent specifications U.S. Pat. Nos. 3,023,253 and 3,064,311 describe flaked L-menthol and a process for the production of such flakes by applying a melt of L-menthol onto a cooled pan roller. If desired, the menthol melt may be introduced between a pair of counter-rotating, cooled rollers. The menthol film that has begun to crystallise on the pan roller is post-processed by tempering it by means of an introduction of heat, and is reinforced by applying additional menthol. Both post-treatments are obtained simultaneously by means of a feed roller. Initially, the flakes such obtained exhibit a good pourability. After longer storage, however, minor caking takes place that requires mechanical loosening by shaking the container. It is noted that such caking is caused by a porous surface that is mentioned but not characterised in more detail, and an accompanying heavy sublimation of the product, and that the product such obtained may be further processed to pellets by compacting.

The principle of further enlargement of the primary particles by compacting is also described in DE 10224087, relating to compacted menthol in the form of menthol pellets as well as a process for the production thereof. Here, however, the focus is not on the effect of the particle size alone, but on the fact that the primary particles must be present in a specific crystal form. On condition that these predominantly consist of the thermodynamically stable α-form that only melts at 42.5° C., it is possible to obtain granular materials that are resistant against caking by compressing crystals obtained from solution crystallisation or from the formation of flakes on cooling rollers.

The subject matter of the international patent application WO 2008 152009 A1 (BASF) is a process for the production of L-menthol in solid form by bringing an L-menthol melt into contact with two cooled surfaces that are spaced apart from one another while the L-menthol melt is congealing, resulting in L-menthol in solid form, whereby the contact between the congealing L-menthol melt and the cooled surfaces is maintained, at least until congelation is completed. In this process, the crystallisation of menthol is effected by a combination of a pre-crystalliser and a double-belt cooler. Herein, the menthol suspension is introduced into the gap between two cooled surfaces and allowed to congeal or to crystallize.

EP 2457554 A1 (SYMRISE) addresses the problems of storage and temperature of L-menthol and D,L-menthol in the range of 0 to 30° C., which are present as crystalline solids and not in liquid form in the mentioned ranges of temperature. As a solution it is suggested to use D,L-isomenthol in a mixture with alkanediol(s) as a means for lowering the melting point of D,L-menthol, optionally in the presence of additional I-menthol.

The subject matter of der WO 2013/171018 A2 (SYMRISE) is a cooling mixture, comprising a phenyl alkenal derivative and a further cooling agent and, optionally, an aroma substance. In this case, menthol or L-menthol are indicated as cooling agents, and menthyl acetate is indicated as an aroma substance.

EP 2033688 A2 (SYMRISE) discloses derivatives of oxalic acid as physiological cooling agents, disclosing in this context that the mixture may contain additional physiological cooling agents such as menthol and menthol derivatives (L-menthol, D-menthol, isomenthol, menthyl acetate, etc.).

The processes of the state of the art share a number of serious disadvantages, namely, particularly, low storage stability. Directly after storing, the products start to agglomerate, needles are formed as a result of sublimation, the crystals break as a result of insufficient mechanical solidity, so that, in all, the product according to the specification is not obtained, which gives rise to various complaints.

The object of the present invention was, therefore, to provide compositions based on menthol which are free from the disadvantages described above and which, particularly, are present in liquid form over a wide range of temperature from about 5 to about 20° C., liquify easily when congealed, at least without sublimation, and are not inferior to menthol in its applicational properties.

DESCRIPTION OF THE INVENTION

The subject matter of the invention is liquid cooling compositions, containing
(a) L-menthol,
(b) D-menthol, and
(c) at least one further cooling agent, selected from the group consisting of isomenthol, menthyl acetate (L), menthyl acetate (D), menthyl acetate (iso), acetic acid menthyl lactate (iso) and acetic acid menthyl lactate (neo),
with the proviso that in case that component (c) represents isomenthol, the compositions do not contain any alkanediols.

Surprisingly, it was found that, by adding the cooling agents forming group (c) to a mixture of the two menthol isomers, a preparation is obtained, which is liquid also at cold temperatures and which has a high storage stability at 20° C. Even mixtures that congeal at very low temperatures dissolve at ambient temperature to form a clear liquid without any sublimation effects. A further advantage is that these mixtures are not inferior to classic menthol, neither in their taste, their odour or their cooling performance, however, they allow a significantly easier processing and, particularly, much easier encapsulation.

Cooling Compositions

The compositions of the invention are particularly characterised in that they contain
(a) about 35 to about 55% by weight L-menthol,
(b) about 25 to about 40% by weight D-menthol, and
(c) about 15 to about 30% by weight isomenthol, menthyl acetate (L), menthyl acetate (D), menthyl acetate (iso), acetic acid menthyl lactate (iso) and acetic acid menthyl lactate (neo) or mixtures thereof.
with the proviso that all quantities add up to 100% by weight.

A first preferred composition contains
(a) L-menthol,
(b) D-menthol, and
(c) menthyl acetate (L),
preferably:
(a) about 50 to about 55% by weight L-menthol,
(b) about 25 to about 35% by weight D-menthol, and
(c) about 18 to about 23% by weight menthyl acetate (L)
with the proviso that all quantities add up to 100% by weight.

A second preferred composition contains
(a) L-menthol,
(b) D-menthol,
(c1) menthyl acetate (L),
(c2) menthyl acetate (D),
(c3) menthyl acetate (iso), and
(c4) acetic acid menthyl acetate (neo, iso)
preferably:
(a) about 50 to about 55% by weight L-menthol,
(b) about 25 to about 35% by weight D-menthol,
(c1) about 8 to about 12% by weight menthyl acetate (L),
(c2) about 8 to about 12% by weight menthyl acetate (D),
(c3) about 0.1 to about 1% by weight menthyl lactate (iso), and
(c4) about 0.1 to about 1% by weight acetic acid menthyl lactate (neo, iso)
with the proviso that all quantities add up to 100% by weight.

A third preferred composition contains
(a) L-menthol,
(b) D-menthol,
(c1) iso-menthol, and
(c2) menthyl acetate (L)
preferably:
(a) about 35 to about 45% by weight L-menthol,
(b) about 35 to about 45% by weight D-menthol,
(c1) about 2 to about 8% by weight iso-menthol, and
(c2) about 15 to about 25% by weight menthyl acetate (L)
with the proviso that all quantities add up to 100% by weight.

A fourth preferred composition contains
(a) L-menthol,
(b) D-menthol,
(c1) iso-menthol,
(c2) menthyl acetate (L),
(c3) menthyl acetate (D),
(c4) menthyl acetate (iso), and
(c5) Acetic acid menthyl acetate (neo, iso)
preferably:
(a) about 35 to about 45% by weight L-menthol,
(b) about 35 to about 45% by weight D-menthol,
(c1) about 2 to about 8% by weight iso-menthol,
(c2) about 8 to about 12% by weight menthyl acetate (L),
(c3) about 8 to about 12% by weight menthyl acetate (D),
(c4) about 0.1 to about 1% by weight menthyl acetate (iso), and
(c5) about 0.1 to about 1% by weight acetic acid menthyl acetate (neo, iso)
with the proviso that all quantities add up to 100% by weight.

Cosmetic, Dermatological and/or Pharmaceutical Compositions

A further aspect of the present invention relates to cosmetic and/or dermatological compositions, containing the above mentioned liquid cooling mixtures, preferably in quantities of about 0.1 to about 10% by weight, more preferably about 0.5 to about 8% by weight, and particularly preferably about 1 to about 5% by weight. The agents may both be skin care, body care or hair care agents, including sun protection agents and oral and tooth care agents as well as (medical) chewing gum. Particularly preferred applications within the range of cosmetic and dermatological compositions are shower baths, shampoos, soaps, air fresheners and the like.

The particularly preferred pharmaceutical compositions include substances for the alleviation of pain of the mucous membranes, specifically cold syrups, sprays, coated tablets and lozenges.

The cosmetic, dermatological and/or pharmaceutical agents may comprise further typical additives and auxiliaries such as, for example, mild surfactants, oil components, emulsifiers, pearlizing waxes, consistency factors, thickeners, superfatting agents, stabilizers, polymers, silicon compounds, fats, waxes, lecithins, phospholipids, UV protection factors, humectants, biogenic agents, antioxidants, deodorants, antiperspirants, anti-dandruff agents, film formers, swelling agents, insect repellents, self-tanning agents, tyrosin inhibitors (depigmentation agents), hydrotropes, solubilizers, preservatives, perfume oils, dyes and the like.

Surfactants

Anionic, non-ionic, cationic and/or amphoteric or zwitterionic surfactants can be comprised as surface-active substances, the portion of which in the means is usually from about 1 to 70, preferably, from 5 to 50 and, particularly, from 10 to 30% by weight. Typical examples of anionic surfactants are soaps, alkyl benzenesulfonates, alkanesulfonates, olefin sulfonates, alkylther sulfonates, glycerol ether sulfonates, α-methyl ester sulfonates, sulfofatty acids, alkyl sulfates, alkyl ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partly oxidized alk(en)yl oligoglycosides or glucoronic acid derivatives, fatty acid-N-alkyl glucamides, protein hydrolyzates (more particularly wheat-based plant products), polyol fatty acid esters, sugar esters, sorbitan esters, polysorbates and amine oxides. If the anionic surfactants contain polyglycol ether chains, they may have a conventional homolog distribution although they preferably have a narrow-range homolog distribution. Typical examples of cationic surfactants are quaternary ammonium compounds such as, for example, dimethyl distearyl ammonium chloride, and esterquats, more particularly quaternized fatty acid trialkanolamine ester salts. Typical examples of amphoteric or zwitterionic surfactants are alkyl betaines, alkyl-amido-betaines, amino-propionates, amino-glycinates, imidazolinium-betaines and sulfo-betaines. All surfactants mentioned are known compounds. Typical examples of particularly suitable mild, i.e. particularly skin-compatible surfactants are fatty alcohol polyglycol ether sulfates, monoglyceride sulphate, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, the latter, preferably, wheat-based proteins.

Oil Components

Suitable oil components are, for example, Guerbet alcohols based on fatty alcohols containing 6 to 18 and preferably 8 to 10 carbon atoms, esters of linear C6-22 fatty acids with linear or branched C6-22 fatty alcohols or esters of branched C6-13 carboxylic acids with linear or branched, C6-22 fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear C6-22 fatty acids with branched alcohols, more particularly 2-ethyl hexanol, esters of C18-38 alkylhydroxycarboxylic acids with linear or branched C6-22 fatty alcohols, more particularly Dioctyl Malate, esters of linear and/or branched fatty acids with polyhydric alcohols (for example, propylene glycol, dimer diol or trimer triol) and/or Guerbet alcohols, triglycerides of C6-C10 fatty acids, liquid mono-, di-, triglyceride mixtures of C6-C18 fatty acids, esters of C6-22 fatty alcohols and/or Guerbet alcohols with aromatic carboxylic acids, more particularly benzoic acid, esters of C2-12 dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched C6-C22-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched C6-C22-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), (ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Suitable emulsifiers are, for example, nonionic surfactants from at least one of the following groups:

products of the addition of 2 to 30 mol ethylene oxide and/or 0 to 5 mol propylene oxide onto linear C8-22 fatty alcohols, onto C12-22 fatty acids, onto alkyl phenols containing 8 to 15 carbon atoms in the alkyl group and onto alkylamines containing 8 to 22 carbon atoms in the alkyl group;

alkyl and/or alkenyl oligoglycosides containing 8 to 22 carbon atoms in the alk(en)yl group and ethoxylated analogs thereof;

addition products of 1 to 15 mol ethylene oxide onto castor oil and/or hydrogenated castor oil;

addition products of 15 to 60 mol ethylene oxide onto castor oil and/or hydrogenated castor oil;

partial esters of glycerol and/or sorbitan with unsaturated, linear or saturated, branched fatty acids containing 12 to 22 carbon atoms and/or hydroxycarboxylic acids containing 3 to 18 carbon atoms and addition products thereof onto 1 to 30 mol ethylene oxide;

partial esters of polyglycerol (average degree of self-condensation 2 to 8), polyethylene glycol (molecular weight 400 to 5.000), trimethylolpropane, pentaerythritol, sugar alcohols (for example, sorbitol), alkyl glucosides (for example, methyl glucoside, butyl glucoside, lauryl glucoside) and polyglucosides (for example, cellulose) with saturated and/or unsaturated, linear or branched fatty acids containing 12 to 22 carbon atoms and/or hydroxycarboxylic acids containing 3 to 18 carbon atoms and addition products thereof onto 1 to 30 mol ethylene oxide;

mixed esters of pentaerythritol, fatty acids, citric acid and fatty alcohol and/or mixed esters of fatty acids containing 6 to 22 carbon atoms, methyl glucose and polyols, preferably glycerol or polyglycerol.

mono-, di- and trialkyl phosphates and mono-, di- and/or tri-PEG-alkyl phosphates and salts thereof;

wool wax alcohols;

polysiloxane/polyalkyl/polyether copolymers and corresponding derivatives;

block copolymers, for example, polyethylene glycol-30 Dipolyhydroxystearate;

polymer emulsifiers, for example, Pemulen types (TR-1, TR-2) of Goodrich or Cosmedia® SP of BASF;

polyalkylene glycols and glycerol carbonate.

Particularly suitable emulsifiers are explained below in more detail:

Alkoxylates.

The addition products of ethylene oxide and/or propylene oxide onto fatty alcohols, fatty acids, alkylphenols or onto castor oil are known commercially available products. They are homolog mixtures of which the average degree of alkoxylation corresponds to the ratio between the quantities of ethylene oxide and/or propylene oxide and substrate with which the addition reaction is carried out. C12/18 fatty acid monoesters and diesters of addition products of ethylene oxide onto glycerol are known as lipid layer enhancers for cosmetic formulation.

Alkyl and/or Alkenyl Oligoglycosides.

Alkyl and/or alkenyl oligoglycosides, their production and their use are known from the prior art. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 moles of ethylene oxide onto the partial glycerides mentioned are also suitable.

Sorbitan Esters.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylolpropane or pentaerythritol with lauric acid, cocofatty acid, tallow fatty acid, palmitic acid, stearic acid, oleic acid, behenic acid and the like optionally reacted with 1 to 30 mol ethylene oxide).

Anionic Emulsifiers.

Typical anionic emulsifiers are aliphatic fatty acids containing 12 to 22 carbon atoms such as, for example, palmitic acid, stearic acid or behenic acid and dicarboxylic acids containing 12 to 22 carbon atoms such as, for example, azelaic acid or sebacic acid.

Amphoteric and Cationic Emulsifiers.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of cocamidopropyl betaine is particularly preferred. Ampholytic surfactants are also suitable emulsifiers. Ampholytic surfactants are surface-active compounds which, in addition to a C8/18 alkyl or acyl group, contain at least one free amino group and at least one —COOH— or —SO3H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and C12/18 acyl sarcosine. Finally, cationic surfactants are also suitable emulsifiers, those of the esterquat type, preferably methyl-quaternized difatty acid triethanolamine ester salts, being particularly preferred.

Fats and Waxes

Typical examples of fats are glycerides, i.e. solid or liquid, vegetable or animal products which consist essentially of mixed glycerol esters of higher fatty acids, suitable waxes are inter alia natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Besides the fats, other suitable additives are fat-like substances, such as lecithins and phospholipids. Lecithins are known among experts as glycerophospholipids which are formed from fatty acids, glycerol, phosphoric acid and choline by esterification. Accordingly, lecithins are also frequently referred to by experts as phosphatidyl cholines (PCs). Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are normally classed as fats. Sphingosines and sphingolipids are also suitable.

Pearlizing Waxes

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as, for example, fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Additional Cooling Agents

Cooling agents are compounds which create a sensation of cold on the skin. These are usually menthol compounds selected from the group consisting of Menthol Methyl Ether, Menthone Glyceryl Acetal (FEMA GRAS[1] 3807), Menthone Glyceryl Ketal (FEMA GRAS 3808), Menthyl Lactate (FEMA GRAS 3748), Menthol Ethylene Glycol Carbonate (FEMA GRAS 3805), Menthol Propylene Glycol Carbonate (FEMA GRAS 3806), Menthyl-N-ethyloxamat, Monomethyl Succinate (FEMA GRAS 3810), Monomenthyl Glutamate (FEMA GRAS 4006), Menthoxy-1,2-propanediol (FEMA GRAS 3784), Menthoxy-2-methyl-1,2-propandiol (FEMA GRAS 3849) and the menthanecarboxylic acid esters and -amides WS-3, WS-4, WS-5, WS-12, WS-14 and WS-30 the mixtures thereof.

[1] FEMA stands for "Flavor and Extracts Manufacturers Association", and GRAS is defined as "Generally Regarded As Safe". A FEMA GRAS denomination means that the substance marked as such has been tested according to standard methods and is considered toxicologically safe.

A first significant representative of these substances is Monomethyl Succinate (FEMA GRAS 3810). Both the succinate and the analogous Monomenthyl Glutamate (FEMA GRAS 4006) are important representative of monomenthyl esters of di- and polycarboxylic acids. Examples of applications of these substances can be found in the specifications WO 2003 043431 (Unilever) or EP 1332772 A1 (IFF).

The next important group of menthol compounds within the meaning of the invention comprises carbonate esters of menthol and polyols such as, for example, glycolene, glycerol or carbohydrates such as, for example, Menthol Ethylenglycol Carbonate (FEMA GRAS 3805=Frescolat® MGC), Menthol Propylenglycol Carbonate (FEMA GRAS 3784=Frescolat® MPC), Menthol 2-Methyl-1,2-propandiol Carbonate (FEMA GRAS 3849) or the corresponding sugar derivatives. Also preferred are the menthol compounds Menthyl Lactate (FEMA GRAS 3748=Frescolat® ML) and, particularly, Menthone Glyceryl Acetal (FEMA GRAS 3807) or Menthone Glyceryl Ketal (FEMA GRAS 3808), which is marketed under the trade name Frescolat® MGA. Particularly preferable among these substances are Menthone Glyceryl Acetal/Ketal and Methyl Lactate as well as Menthol Ethylene Glycol Carbonate or Menthol Propylene Glycol Carbonate which are marketed by the applicant under the trade names Frescolat® MGA, Frescolat® ML, Frescolat® MGC and Frescolat® MPC.

Menthol compounds which have a C—C bond in the 3-position were developed for the first time in the 1970ies. Of these, also a number of representatives within the meaning of the invention may be used. These substances are generally referred to as WS types. A menthol derivative forms the base body where the hydroxyl group is replaced by a carboxyl group (WS-1). All other WS types are derived from this structure WS, such as, for example, the preferred species within the meaning of the invention WS-3, WS-4, WS-5, WS-12, WS-14 and WS-30.

Consistency Factors and Thickeners

Suitable consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used. Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, also relatively high molecular weight polyethylene glycol monoesters and diesters of fatty acids, polyacrylates (for example, Carbopols® and Pemulen types [Goodrich]; Synthalens® [Sigma]; Keltrol types [Kelco]; Sepigel types [Seppic]; Salcare types [Allied Colloids]), polyacrylamides, polymers, polyvinyl alcohol and polyvinyl pyrrolidone. Other consistency factors which have proved to be particularly effective are bentonites, for example, Bentone® Gel VS5PC (Rheox) which is a mixture of cyclopentasiloxane, Disteardimonium Hectorite and propylene carbonate. Other suitable consistency factors are surfactants such as, for example, ethoxylated fatty acid glycerides, esters of fatty acids with polyols, for example, pentaerythritol or trimethylol propane, narrow-range fatty alcohol ethoxylates or alkyl oligoglucosides and electrolytes, such as sodium chloride and ammonium chloride.

Superfatting Agents and Stabilizers

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Metal salts of fatty acids such as, for example, magnesium, aluminium and/or zinc stearate or ricinoleate may be used as stabilizers.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, GrUnau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example, dibromobutane, with bis-dialkylamines, for example, bisdimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Silicone Compounds

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates.

UV Protection Factors

UV protection factors are, for example, organic substances (light filters) which are liquid or crystalline at room temperature and which are capable of absorbing ultraviolet radiation and of releasing the energy absorbed in the form of longer-wave radiation, for example, heat. UV protection factors are usually present in amounts of 0.1 to 5 and preferably of 0.2 to 1% by weight. UV-B filters can be oil-soluble or water-soluble. The following are examples of oil-soluble substances:

3-benzylidene camphor or 3-benzylidene norcamphor and derivatives thereof, for example, 3-(4-methylbenzylidene)-camphor;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and cctyl triazone or cioctyl butamido triazone (Uvasorb® HEB);

propane-1,3-diones such as, for example, 1-(4-tert.butylphenyl)-3-(4'-methoxyphenyl)-propane-1,3-dione);

ketotricyclo(5.2.1.0)decane derivatives.

Suitable water-soluble substances are:

2-phenylbenzimidazole-5-sulfonic acid and alkali metal, alkaline earth metal, ammonium, alkylammonium, alkanolammonium and glucammonium salts thereof;

1H-benzimidazole-4,6-disulfonic acid, 2,2'-(1,4-phenylene)bis-, disodium salt (Neo Heliopan® AP)

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol® 1789), 2-(4-diethylamino-2-hydroxybenzoyl)-benzoic acid hexylester (Uvinul® A Plus), 1-phenyl-3-(4'-isopropylphenyl)-propane-1,3-dione and enamine compounds. The UV-A and UV-B filters may of course also be used in the form of mixtures. Particularly favourable combinations consist of the derivatives of benzoyl methane, for example, 4-tert.butyl-4'-methoxydibenzoylmethane (Parsol® 1789) and 2-cyano-3,3-phenylcinnamic acid-2-ethyl hexyl ester (Octocrylene) in combination with esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example, Titandioxid T 805 (Degussa) and Eusolex® T2000, Eusolex® T, Eusolex® T-ECO, Eusolex® T-S, Eusolex® T-Aqua, Eusolex® T-45D (all by Merck), Uvinul $TiO_2$ (BASF). Suitable hydrophobic coating materials are, above all, silicones and, among these, especially trialkoxyoctylsilanes or simethicones. So-called micro- or nanopigments are preferably used in sun protection products. Micronized zinc oxide such as, for example, ZCOTE® or Z-COTE HP1® is preferably used.

Humectants

Humectants contribute towards improving the sensory properties of the composition and serve to regulate the skin moisture level. In addition, they can contribute towards improving the cold stability of the compositions according to the invention, particularly when emulsions are concerned. The humectants are normally present in a quantity of 0.1 to 15% by weight, preferably 1 to 10% by weight and more particularly 5 to 10% by weight.

According to the invention, suitable humectants are inter alia amino acids, pyrrolidone carboxylic acid, lactitol, urea and urea derivatives, uric acid, glucosamine, creatinine, cleavage products of collagen, chitosan or chitosan salts/derivatives and, in particular, polyols and polyol derivatives (for example, glycerol, diglycerol, triglycerol, ethylene glycol, propylene glycol, butylene glycol, erythritol, 1,2,6-hexanetriol, polyethylene glycols, such as PEG-4, PEG-6, PEG-7, PEG-8, PEG-9, PEG-10, PEG-12, PEG-14, PEG-16, PEG-18, PEG-20), sugars and sugar derivatives (inter alia fructose, glucose, maltose, maltitol, mannitol, inositol, sorbitol, sorbityl silanediol, sucrose, trehalose, xylose, xylitol, glucuronic acid and salts thereof), ethoxylated sorbitol (Sorbeth-6, Sorbeth-20, Sorbeth-30, Sorbeth-40), honey and hydrogenated honey, hydrogenated starch hydrolyzates and mixtures of hydrogenated wheat protein and PEG-20-acetate copolymer. According to the invention, particularly preferred humectants are glycerol, diglycerol, triglycerol and butylenglycol.

Biogenic Agents and Antioxidants

Biogenic agents are, for example, tocopherol, tocopherol acetate, tocopherol palmitate, ascorbic acid, (desoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example, *prunus* extract, bambara nut extract, and vitamin complexes.

Antioxidants interrupt the photo-chemical reaction chain which is triggered as soon as UV radiation penetrates the skin. Typical examples are amino acids (for example, glycine, histidine, tyrosine, tryptophane) and derivatives thereof, imidazoles (for example, urocanic acid) and derivatives thereof, peptides, such as D,L-carnosine, D-carnosine, L-carnosine and derivatives thereof (for example, anserine), carotinoids, carotenes (for example, α-carotene, β-carotene, lycopene) and derivatives thereof, chlorogenic acid and derivatives thereof, liponic acid and derivatives thereof (for example, dihydroliponic acid), aurothioglucose, propylthiouracil and other thiols (for example, thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example, butionine sulfoximines, homocysteine sulfoximine, butionine sulfones, penta-, hexa- and hepta-thionine sulfoximine) in very small compatible dosages) (for example, μmol to μmol/kg), also (metal) chelators (for example, α-hydroxyfatty acids, palmitic acid, phytic acid, lactoferrine), α-hydroxy acids (for example, citric acid, lactic acid, malic acid), humic acid, bile acid, bile extracts, bilirubin, biliverdin, EDTA, EGTA and derivatives thereof, unsaturated fatty acids and derivatives thereof (for example, γ-linolenic acid, linoleic acid, oleic acid), folic acid and derivatives thereof, ubiquinone and ubiquinol and derivatives thereof, vitamin C and derivatives thereof (for example, ascorbyl palmitate, Mg ascorbyl phosphate, ascorbyl acetate), tocopherols and derivatives (for example, vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (for example, ZnO, ZnSO4), selenium and derivatives thereof (for example, selenium methionine), stilbenes and derivatives thereof (for example, stilbene oxide, trans-stilbene oxide) and derivatives of these active substances suitable for the purposes of the invention (salts, esters, ethers, sugars, nucleotides, nucleosides, peptides and lipids).

Deodorants and Germ Inhibitors

Cosmetic deodorants counteract, mask or eliminate body odors. Body odors are formed through the action of skin bacteria on apocrine perspiration which results in the formation of unpleasant-smelling degradation products. Accordingly, deodorants contain active principles which act as germ inhibitors, enzyme inhibitors, odor absorbers or odor maskers.

Germ Inhibitors.

Basically, suitable germ inhibitors are any substances which act against gram-positive bacteria such as, for example, 4-hydrobenzoic acid and salts and esters thereof, N-(4-chlorophenyl)-N'-(3,4-dichlorophenyl)-urea, 2,4,4'-trich loro-2'-hydroxydiphenylether (triclosan), 4-chloro-3,5-dimethylphenol, 2,2'-methylene-bis(6-bromo-4-chlorophenol), 3-methyl-4-(1-methylethyl)-phenol, 2-benzyl-4-chlorophenol, 3-(4-chlorophenoxy)-propane-1,2-diol, 3-iodo-2-propinyl butyl carbamate, chlorhexidine, 3,4,4'-trichlorocarbanilide (TTC), antibacterial perfumes, thymol, thyme oil, eugenol, clove oil, menthol, mint oil, farnesol, phenoxyethanol, glycerol monocaprinate, glycerol monocaprylate, glycerol monolaurate (GML), diglycerol monocaprinate (DMC), salicylic acid-N-alkylamides such as, for example, salicylic acid-n-octylamide or salicylic acid-n-decylamide.

Enzyme Inhibitors.

Suitable enzyme inhibitors are, for example, esterase inhibitors. Esterase inhibitors are preferably trialkyl citrates such as trimethyl citrate, tripropyl citrate, triisopropyl citrate, tributyl citrate and, in particular, triethyl citrate (Hydagen® CAT). Esterase inhibitors inhibit enzyme activity and thus reduce odor formation. Other esterase inhibitors are sterol sulfates or phosphates such as, for example, lanosterol, cholesterol, campesterol, stigmasterol and sitosterol sulfate or phosphate, dicarboxylic acids and esters thereof such as, for example, glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof such as, for example, citric acid, malic acid, tartaric acid or tartaric acid diethyl ester, and zinc glycinate.

Odor Absorbers.

Suitable odor absorbers are substances which are capable of absorbing and largely retaining odor-forming compounds. They reduce the partial pressure of the individual components and thus also reduce the rate at which they spread. Odor absorbers should not affect the perfume note of a perfume. Odor absorbers are not active against bacteria. Odor absorbers contain, for example, a complex zinc salt of ricinoleic acid, or special perfumes of largely neutral odors known to the expert as "fixateurs" such as, for example, extracts of *ladanum* or *styrax* or certain abietic acid derivatives as their principal component. Odor maskers are perfumes or perfume oils which, besides their odor-masking function, impart their particular perfume note to the deodorants. Suitable perfume oils are, for example, mixtures of natural and synthetic perfumes. Natural perfumes include the extracts of blossoms, stems and leaves, fruits, fruit peel, roots, woods, herbs and grasses, needles and branches, resins and balsams. Animal raw materials, for example, civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, lemon balm oil, mint oil, cinnamon leaf oil, lime-blossom oil, juniper berry oil, vetiver oil, olibanum oil, *galbanum* oil, *ladanum* oil and lavendin oil. The following are preferably used either individually or in the form of mixtures: bergamot oil, dihydromyrcenol, lilial, lyral, citronellol, phenylethyl alcohol, ahexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Antiperspirants.

Antiperspirants reduce perspiration and thus counteract underarm wetness and body odor by influencing the activity of the eccrine sweat glands. Aqueous or water-free antiperspirant formulations typically contain the following ingredients:

astringent active principles,
oil components,
nonionic emulsifiers,
co-emulsifiers,
consistency factors, auxiliaries in the form of, for example, thickeners or complexing agents and/or
non-aqueous solvents such as, for example, ethanol, propylene glycol and/or Glycerol.

Suitable astringent active principles of antiperspirants are, above all, salts of aluminium, zirconium or zinc. Suitable antihydrotic agents of this type are, for example, aluminium chloride, aluminium chlorohydrate, aluminium dichlorohydrate, aluminium sesquichlorohydrate and complex compounds thereof, for example, with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, for example, with amino acids, such as glycine. Oil-soluble and water-soluble auxiliaries typically encountered in antiperspirants may also be present in relatively small amounts. Oil-soluble auxiliaries such as these include, for example:

inflammation-inhibiting, skin-protecting or pleasant-smelling essential oils,
synthetic skin-protecting agents and/or
oil-soluble perfume oils.

Typical water-soluble additives are, for example, preservatives, water-soluble perfumes, pH adjusters, for example, buffer mixtures, water-soluble thickeners, for example, water-soluble natural or synthetic polymers such as, for example, xanthan gum, hydroxyethyl cellulose, polyvinyl pyrrolidone or high molecular weight polyethylene oxides Film Formers Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Swelling Agents

Suitable swelling agents for aqueous phases are montmorillonites, clay minerals, Pemulen and alkyl-modified Carbopol types (Goodrich). Other suitable polymers or swelling agents can be found in R. Lochhead's review in Cosm. Toil. 108, 95 (1993).

Insect Repellents

Suitable insect repellents are N,N-diethyl-m-toluamide, pentane-1,2-diol and ethyl butyl acetylaminopropionate. A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Ingredients for Oral and Dental Care Products

In general, tooth pastes and tooth cremes are usually understood to be gel or pasty compositions of water, thickeners, moisturizers, abrasives or cleaning agents, surfactants, sweeteners, flavours, deodorizing agents and agents against oral and dental conditions. Tooth pastes according to the invention may comprise any typical cleaning agents such as, for example, chalk, dicalcium phosphate, insoluble sodium metaphosphate, aluminium silicates, calcium pyrophosphate, fine-particle synthetic resins, silicic acids, aluminium oxide and aluminiumoxide trihydrate.

Particularly suitable cleaning agents for the tooth pastes of the invention are, preferably, fine-particle silicic acid xerogels, silicic acid hydrogels, precipitation silicic acids, aluminiumoxide trihydrate and fine-particle alpha-aluminiumoxide or mixtures of said cleaning agents in quantities of 15 to 40% by weight of the tooth paste. Suitable moisturizers are, preferably, low-molecular polyethylene glycols, glycerol, sorbit or mixtures of these products in quantities of up to 50% by weight. Suitable known thickeners are the thickening, fine-particle gel silicic acids and hydrocolloids such as, for example, carboxymethyl cellulose, hydroxyethyl cellulose, hydroxypropyl guar, hydroxyethyl starch, polyvinyl pyrrolidone, highmolecular polyethylene glycol, vegetable gums such as gum tragacanth, agar-agar, carrageen moss, gum *arabicum*, xantham gum and carboxyvinyl polymers (for example, Carbopol® types). In addition to the mixtures of menthofuran and menthol compounds, the oral and dental care products may comprise, in particular, surface-active substances, preferably, anionic and nonionic high-foam surfactants like the substances mentioned above, particularly, alkylether sulphate salts, alkyl polyglucosides and their mixtures.

Further common additives to tooth pastes are:
preservatives and anti-bacterial agents such as, for example, p-hydroxybenzoic acid methyl/ethyl or propyl esters, sodium sorbate, sodium benzoate, bromochlorophene, phenyl salicylic acid esters, thymol and the like;
anticalculus agents, such as organophosphates, for example, 1-hydroxyethane-1,1-diphosphonic acid, 1-phosphonopropane-1,2,3-tricarboxylic acid and others, which are known, for example, from U.S. Pat. No. 3,488,419, DE 2224430 A1 and DE 2343196 A1;
other anti-cariogenic substances such as, for example, sodium fluoride, sodium monofluorophosphate, tin fluoride;
sweeteners such as, for example, saccharin sodium, sodium cyclamate, sucrose, lactose, maltose, fructose or Apartame® (methyl L-α-aspartyl-L-phenylalaninate), *stevia* extracts and their sweetening compounds, particularly, rebaudiosides;
additional aromas such as, for example, *eucalyptus* oil, aniseed oil, fennel oil, caraway oil, methyl acetate, cinnamon aldehyde, anethole, vanillin, thymol and mixtures of these and other natural and synthetic aromas;
pigments such as, for example, titanium dioxide;
dyes;
buffer substances such as, for example, primary, secondary or tertiary alkali phosphates or citric acid/sodium citrate;
wound-healing and inflammation-inhibiting substances such as, for example, allantoin, urea, azulene, chamomile active ingredients and derivatives of acetylsalicylic acid.

A preferred form of embodiment of the cosmetic compositions are tooth pastes in form of an aqueous, pasty dispersion, comprising polishing agents, moisturizers, viscosity regulators and, optionally, further common components, as well as the mixture of mentho furane and menthol compounds in amounts from 0.5 to 2% by weight.

In mouthwashs, a combination with hydroalcoholic solutions of differing degrees of essential oils, emulsifiers, astringent and toning drug extracts, calculus-inhibiting agents, antibacterial additives and flavour correctants is easily possible. Another preferred embodiment of the invention is a mouthwash in the form of an aqueous or a hydroalcoholic solution, comprising the mixture of menthofuran and menthol compounds in amounts from 0.5 to 2% by weight. In mouthwash compositions which are thinned before application higher concentrations may yield sufficient effects corresponding to the intended thinning ratio.

Hydrotropes

In addition, hydrotropes, for example, ethanol, isopropyl alcohol or polyols, may be used to improve flow behaviour; these substances mostly correspond to the carriers stated above. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 dalton;
technical oligoglycerol mixtures with a degree of self-condensation of 1.5 to 10 such as, for example, technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example, methyl and butyl glucoside;
sugar alcohols containing 5 to 12 carbon atoms, for example, sorbitol or mannitol,
sugars containing 5 to 12 carbon atoms, for example, glucose or sucrose;
amino sugars, for example, glucamine;
dialcoholamines, such as diethanolamine or 2-aminopropane-1,3-diol.

Preservatives

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Perfume Oils and Aromas

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, *angelica*, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), and resins and balsams (*galbanum*, elemi, benzoin, myrrh, olibanum, opoponax). Also suitable are animal products, such as, for example, civet and castoreum. Typical synthetic fragrance compounds are products of the ester, ether, aldehyde, ketone, alcohol, and hydrocarbon type. Examples of perfume compounds of the ester type are benzyl acetate, phenoxyethyl isobutyrate p-tert.butyl cyclohexylacetate, linalyl acetate, dimethyl benzyl carbinyl acetate, phenyl ethyl acetate, linalyl benzoate, benzyl formate, ethyl methyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal, the ketones include the ionones, α-isomethyl ionone and methyl cedryl ketone, the alcohols include anethol, citronellol, eugenol, isoeugenol, geraniol, linalool, phenylethyl alcohol and and terpineol, the hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components, for example, sage oil, camomile oil, clove oil, lemon balm oil, mint oil, cinnamon leaf oil, lime-blossom oil, juniper berry oil, vetiver oil, olibanum oil, *galbanum* oil, *ladanum* oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Suitable aromas are, for example, peppermint oil, spearmint oil, aniseed oil, Japanese anise oil, caraway oil, *eucalyptus* oil, fennel oil, citrus oil, wintergreen oil, clove oil, menthol and the like.

Dyes

Suitable dyes are any of the substances suitable and approved for cosmetic purposes, as compiled, for example, in the publication "Kosmetische Färbemittel" ("Cosmetic Dyes") by the Farbstoffkommission der Deutschen Forschungsgesellschaft (The Dyes Commission of the German Research Association), Verlag Chemle, Weinheim, 1984, pp. 81-106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. These dyes are normally used in concentrations of 0.001 to 0.1% by weight, based on the mixture as a whole.

The total portion of additives and auxiliaries can be from 1 to 50, preferably from 5 to 40% by weight—based on the means. The means can be produced by conventional cold or hot processes; preferably, the phase inversion temperature method is applied.

Chewing Gums

The preferred oral compositions can be (medical) chewing gums. These products typically contain a water-insoluble and a water-soluble component.

The water-insoluble base, which is also referred to as "gum base", typically comprises natural or synthetic elastomers, resins, fats and oils, plasticizers and softeners, fillers, dyes and optionally waxes. The base normally makes up 5 to 95% by weight, preferably 10 to 50% by weight, and more particularly 20 to 35% by weight of the composition as a whole. In one typical form of embodiment of the invention, the base is composed of between 20 and 60% by weight synthetic elastomers, 0 to 30% by weight natural elastomers, 5 to 55% by weight plasticizers, 4 to 35% by weight fillers, and in small amounts additives such as dyes, antioxidants and the like, with the proviso that they are water-soluble only in small amounts, if at all.

Suitable synthetic elastomers are, for example, polyisobutylenes with average molecular weights (as measured by GPC) of 10,000 to 100,000 and preferably 50,000 to 80,000, isobutylen/isoprene copolymers ("butyl elastomers"), styrene/butadiene copolymers (styrene:butadiene ratio, for example, 1:3 to 3:1), polyvinyl acetates with average molecular weights (as measured by GPC) of 2,000 to 90,000 and preferably 10,000 to 65,000, polyisoprenes, poly-ethylenes, vinyl acetate/vinyl laurate copolymers and mixtures thereof. Examples of suitable natural elastomers are rubbers such as, for example, smoked or liquid latex or guayuls, and natural gums, such as jelutong, lechi caspi, perillo, sorva, massaranduba balata, massaranduba chocolate, nispero, rosindinba, chicle, gutta hang kang and mixtures thereof. The choice of the synthetic and natural elastomers and their mixing ratios essentially depends on whether or not bubbles are to be produced with the chewing gums ("bubble gums"). Elastomer mixtures containing jelutong, chicle, sorva and massanduraba are preferably used.

In most cases, the elastomers are too hard or lack plasticity for satisfactory processing, so it has been found to be of advantage to use special plasticizers which, of course, must also satisfy, in particular, all requirements relating to their being allowed as food additives. In this respect, esters of resin acids are particularly suitable, for example, esters of lower aliphatic alcohols or polyols with wholly or partly hydrogenated, monomeric or oligomeric resin acids. In particular, the methyl, glycerol or pentaerythritol esters or mixtures thereof are used for this purpose. Alternatively, terpene resins, which can be derived from α-pinene, β-pinene, δ-limonene or mixtures thereof, can also be used.

Suitable fillers or texturizers are magnesium or calcium carbonate, ground pumice stone, silicates, especially magnesium or aluminium silicates, clays, aluminium oxides, talcum, titanium dioxide, mono-, di- and tricalcium phosphate and cellulose polymers.

Suitable emulsifiers are tallow, hydrogenated tallow, hydrogenated or partly hydrogenated vegetable oils, cocoa butter, partial glycerides, lecithin, triacetin and saturated or unsaturated fatty acids containing 6 to 22 and preferably 12 to 18 carbon atoms and mixtures thereof.

Suitable colourants and whiteners are, for example, the FD and C types approved for use in foods, plant and fruit extracts and titanium dioxide.

The gum bases may contain waxes or be wax-free; examples of wax-free compositions can be found inter alia in U.S. Pat. No. 5,286,500, the disclosure of which is specifically referred to herein.

In addition to the water-insoluble gum base, chewing gum compositions regularly comprise a water-soluble portion, consisting, for example, of softeners, sweeteners, fillers, flavourings, flavour enhancers, emulsifiers, colourants, acidifiers, antioxidants and the like, here with the proviso that the constituents are at least sufficiently water-soluble. Depending on the water-solubility of the particular representatives, individual constituents may thus be both part of the water-insoluble and the water-soluble phase. It is, however, also possible to use combinations of, for example, one water-soluble and one water-insoluble emulsifier, in which case the individual representatives are present in different phases. The water-insoluble component usually makes up 5 to 95% by weight and, preferably, 20 to 80% by weight of the composition.

Water-soluble softeners or plasticizers are added to the chewing gum compositions to improve chewability and the chewing feel, and are present in the mixtures in quantities of typically 0.5 to 15% by weight. Typical examples are glycerol, lecithin and aqueous solutions of sorbitol, hydrogenated starch hydrolysates or corn syrup.

Suitable sweeteners are both sugar-containing or sugar-free compounds which are used in quantities of 5 to 95% by weight, preferably in quantities of 20 to 80% b weight and more particularly in quantities of 30 to 60% by weight, based on the chewing gum composition. Typical saccharide sweeteners are sucrose, dextrose, maltose, dextrin, dried invert sugar, fructose, fructose, levulose, galactose, corn syrup and mixtures thereof. Suitable sugar substitutes are sorbitol, mannitol, xylitol, hydrogenated strarch hydrolysates, maltitol and mixtures thereof. Further suitable additives are so-called high-intensity artificial sweeteners (HIAS) such as, for example, sucralose, aspartame, acesulfam salts, alitam, saccharin and saccharin salts, cyclamic acid and salts thereof, glycyrrhicins, dihydrochalcones, thaumatin, monellin and the like either individually or in the form of mixtures. The hydrophobic HIAS, which are the subject of the international patent application WO 2002 091849 A1 (Wrigleys), are also particularly effective, as well as *stevia* extracts and their active ingredients, particularly, ribaudioside A. The quantity in which these substances are used is primarily determined by their intensity and is typically in the range from 0.02 to 8% by weight.

Fillers are particularly suitable for the production of low-calorie chewing gums and may be selected, for example, from polydextrose, raftilose, rafitilin, fructo-oligosaccharides (NutraFlora), palatinose oligosaccharides, guar gum hydrolysates (Sun Fiber) and dextrins.

The choice in flavourings is virtually unlimited and is not critical to the essence of the invention. They normally make up 0.1 to 15% by weight and preferably 0.2 to 5% by weight of the chewing gum composition. Suitable flavourings are, for example, essential oils, synthetic aromas and the like, such as, for example, aniseed oil, Japanese anise oil, caraway oil, *eucalyptus* oil, fennel oil, citrus oil, wintergreen oil, clove oil and the like, such as used, for example, in oral and dental care products.

The chewing gums may further comprise auxiliaries and additives, which are suitable, for example, for dental care, more particularly for controlling plaque and gingivitis, such as, for example, chlorhexidine, CPC or triclosan. They may also contain pH adjusters (for example, buffers or urea), anti-caries agents (for example, phosphates or fluorides), biogenic agents (antibodies, enzymes, caffeine, plant extracts), providing these substances are permitted in foods and do not undesirably interact with one another.

Capsules

In another embodiment, the invention also relates to capsules containing the liquid cooling compositions described above.

The compositions are typically encapsulated by means of solid coating materials such as, for example, starches, including their degradation products as well as chemically or physically produced derivatives (more particularly, dextrins and maltodextrins) and mixtures of two or more of the following substances: gelatin, gum arabic, agar-agar, ghatti gum, gellan gum, modified and non-modified celluloses, pullulan, curdlan, carrageenan, alginic acid, pectin, inulin, xanthan gum.

The solid encapsulating material is, preferably, a gelatin (more particularly, porcine, bovine, poultry and/or fish gelatin), which, preferably, has a swelling factor of more than or equal to 20, more particularly, of more than or equal to 24. Also preferred are maltodextrins (more particularly, on the basis of cereal, specifically maize, wheat, tapioca or potatoes), which preferably have DE values within the range of 10 to 20. Also preferred are celluloses (for example, cellulose ethers), alginates (for example, sodium alginate), carrageenan (for example, beta, iota, lambda and/or kappa carrageenan), gum arabic, curdlan and/or agar agar.

Among these substances, gelatin is particularly preferred, as it is readily available and different swelling factors of gelatin may be purchased. Particularly preferred, particularly for oral applications, are seamless gelatin or alginate capsules, the membrane of which very quickly dissolves or breaks open in the mouth or when chewed. Corresponding capsules are disclosed in detail, for example, in EP 0389700 A1, U.S. Pat. Nos. 4,251,195, 6,214,376, WO 2003 055587 or WO 2004 050069 A1.

"Microcapsules" or "nanocapsules" are understood by the expert to be spherical aggregates with a diameter of about 0.0001 to about 5 mm and preferably 0.005 to 0.5 mm, which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, molten waxes are absorbed in a matrix ("microsponge") which, as microparticles, may be additionally coated with film-forming polymers. According to a third process, particles are alternatingly coated with polyelectrolytes of different charges ("layer-by-layer" method). The microscopically small capsules can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agarose, maltodextrins, alginic acid and salts thereof, for example, sodium or calcium alginate, fats and fatty acids, cetyl alcohol, collagen, chitosan, lecithins, gelatin, albumin, shellac, polysaccharides such as starch or dextran, polypeptides, protein hydrolyzates, sucrose and waxes. Semisynthetic membrane materials are inter alia chemically modified celluloses, more particularly cellulose esters and ethers, for example, cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers such as polyacrylate, polyamide, polyvinyl alcohol or polyvinyl pyrrolidone.

Examples of state of the art microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicerin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids) as well as Primaspheres and Primasponges (chitosan, alginates) and Primasys (phospholipids).

Microcapsules made of chitosan and processes for their production are well known from the state of the art [WO 01/01926, WO 01/01927, WO 01/01928, WO 01/01929]. Microcapsules having mean diameters in the range from 0.0001 to 5, preferably 0.001 to 0.5 and particularly preferably 0.005 bis 0.1 mm, consisting of a coating membrane and a matrix containing the active agents, may be obtained, for example, by (a) preparing a matrix composed of gel formers, cationic polymers and active agents, (b) optionally, dispersing the matrix in an oil phase, (c) treating the dispersed matrix with aqueous solutions of anionic polymers, optionally removing the oil phase in this process.

Here, steps (a) and (c) are exchangeable insofar that anionic polymers are used instead of the cationic polymers, and vice versa.

It is also possible to produce the capsules by coating the capsules in alternating layers of differently charged polyelectrolytes (layer-by-layer method). In this context, it is referred to the European patent EP 1064088 B1 (Max-Planck-Gesellschaft).

INDUSTRIAL APPLICATION

A further subject matter of the present invention relates to a non-therapeutic process for cooling and soothing the skin or the mucuous membranes by bringing these into contact with a quantity of the liquid cooling compositions. This may be particularly accomplished by topically applying any one of the previously described cosmetic compositions.

Lastly, the invention also relates to the use of the liquid cooling compositions for the production of cosmetic and/or dermatological and/or pharmaceutical compositions in the manner described above in more detail.

EXAMPLES

Examples 1 to 4, Comparison Example V1

Various mixtures of cooling agents were prepared and stored at 5° C. or 20° C., respectively. The composition of the mixtures and their storage behaviour is reflected in Table 1:

TABLE 1

Storage behaviour of mixtures of cooling agents

| | 1 | 2 | 3 | 4 | V1 |
|---|---|---|---|---|---|
| Component | | | | | |
| L-Menthol | 52.00 | 52.00 | 38.00 | 38.00 | 50.00 |
| D-Menthol | 28.00 | 28.00 | 38.00 | 38.00 | 50.00 |
| Iso-Menthol | — | — | 4.00 | 4.00 | — |
| Menthyl acetate (L) | 20.00 | 9.50 | 20.00 | 9.50 | — |
| Menthyl acetate (D) | — | 9.50 | — | 9.50 | — |
| Menthyl acetate (iso) | — | 0.60 | — | 0.60 | — |
| Acetic acid menthyl acetate | — | 040 | — | 0.40 | — |
| Storage behaviour | | | | | |
| Directly after preparation | liquid | liquid | liquid | liquid | solid |
| 1 day, 20° C. | liquid | liquid | liquid | liquid | solid |
| 1 day, 5° C. | liquid | liquid | liquid | liquid | solid |
| 5 days, 20° C. | liquid | liquid | liquid | liquid | solid |

The examples and comparison examples prove the superiority of the compositions of the invention, which were present in liquid form both in cold conditions and at ambient temperature, while the mixture of the two menthol isomers is solid. In addition, the new mixtures proved to be fully equivalent to menthol with regard to its taste, its odour and its cooling capability.

The invention claimed is:

1. A liquid composition comprising
   (a) about 50 to about 55% by weight L-menthol,
   (b) about 25 to about 35% by weight D-menthol, and
   (c) about 18 to about 23% by weight menthyl acetate (L),
   with the proviso that all quantities add up to 100% by weight.

2. A sec-end liquid composition, comprising
   (a) about 50 to about 55% by weight L-menthol,
   (b) about 25 to about 35% by weight D-menthol,
   (c1) about 8 to about 12% by weight menthyl acetate (L),
   (c2) about 8 to about 12% by weight menthyl acetate (D),
   (c3) about 0.1 to about 1% by weight menthyl lactate (iso), and
   (c4) about 0.1 to about 1% by weight acetic acid menthyl lactate (neo),
   with the proviso that all quantities add up to 100% by weight.

3. A liquid composition comprising
   (a) about 35 to about 45% by weight L-menthol,
   (b) about 35 to about 45% by weight D-menthol,
   (c1) about 15 to about 25% by weight menthyl acetate (L), and
   (c2) about 2 to about 8% by weight isomenthol,
   with the proviso that all quantities add up to 100% by weight.

* * * * *